United States Patent [19]
Ridker et al.

[11] Patent Number: 6,040,147
[45] Date of Patent: Mar. 21, 2000

[54] SYSTEMIC INFLAMMATORY MARKERS AS DIAGNOSTIC TOOLS IN THE PREVENTION OF ATHEROSCLEROTIC DISEASES AND AS TOOLS TO AID IN THE SELECTION OF AGENTS TO BE USED FOR THE PREVENTION AND TREATMENT OF ATHEROSCLEROTIC DISEASE

[75] Inventors: Paul Ridker, Chestnut Hill; Charles H. Hennekens, South Natick, both of Mass.

[73] Assignee: The Brigham and Women's Hospital, Inc., Boston, Mass.

[21] Appl. No.: 09/054,212

[22] Filed: Apr. 2, 1998

Related U.S. Application Data

[60] Provisional application No. 60/043,039, Apr. 2, 1997, provisional application No. 60/041,950, Apr. 2, 1997, and provisional application No. 60/070,894, Jan. 9, 1998.

[51] Int. Cl.$^7$ .......................... G01N 33/53; G01N 33/68
[52] U.S. Cl. .................. 435/7.24; 435/7.92; 435/7.93; 436/71; 436/86; 436/811
[58] Field of Search ................................. 435/7.24, 7.92, 435/7.93; 436/71, 86, 811

[56] References Cited

U.S. PATENT DOCUMENTS

| | | | |
|---|---|---|---|
| 4,902,630 | 2/1990 | Bennett et al. | 436/546 |
| 5,003,065 | 3/1991 | Merritt et al. | 540/469 |
| 5,272,258 | 12/1993 | Siegel et al. | 530/388.25 |
| 5,500,345 | 3/1996 | Soe et al. | 435/71 |

OTHER PUBLICATIONS

Ridker et al, New England, Journ. Med. 336, 973–974, 1997.
Kuller L.H., et al., "Relation of C–Reactive Protein and Coronary Heart Disease in the MRFIT Nested Case–Control Study", *Am J Epidemiol.* (1996), 144:537–547.
Haverkate, F., et al., "Production of C–Reactive Protein and Risk of Coronary Events in Stable and Unstable Angina", *Lancet*, (1997), 349:462–466.
Lagrand, W.K., et al., "C–Reactive Protein Colocalizes with Complement in Human Hearts During Acute Myocardial Infarction", (1997), *Circulation*, 95:97–103.
Paul M. Ridker et al., "Plasma concentration of soluble intercellular adhesion molecule 1 and risks of future myocardial infarction in apparently healthy men," *The Lancet*, vol. 351, No. 9096, pp. 88–92, Jan. 10, 1988.
M A Mendall et al, "C Reactive protein and its relation to cardiovascular risk factors' a population based cross sectional study," *BMJ*, vol. 312, pp. 1065–1069, Feb. 1996.
Russell P Tracy et al, "Relationship of C–Reactive Protein to Risk of Cardiovascular Disease in the Elderly," *Arteriosclerosis, Thrombosis, and Vascular Biology*, vol. 17, No. 6 pp. 1121–1127, Jun. 1997.
Paul M Ridker et al, "Plasma Concentration of C–Reactive Protein and Risk of Developing Peripheral Vascular Disease," *Circulation*, vol. 97, pp. 425–428, 1998.
Paul M. Ridker et al., "C–Reactive Protein Adds to the Predictive Value of Total and HDL Cholesterol in Determining Risk of First Myocardial Infarction," *Circulation*, vol. 97, pp. 2007–2011, 1998.
Wolfgang Koenig, M.D., "C–Reactive Protein, a Sensitive Marker of Inflammation, Predicts Future Risk of Coronary Heart Disease in Initially Healthy Middle–Aged Men," *Circulation*, vol. 99, pp. 237–242, 1999.
Paul M. Ridker et al., "Prospective Study of C–Reactive Protein and the Risk of Future Cardiovascular Events Among Apparently Healthy Women," *Circulation*, vol. 98, pp. 731–733, 1998.
Paul M. Ridker et al., "Inflammation, Pravastatin, and the Risk of Coronary Events After Myocardial Infarction in Patients With Average Cholesterol Levels," *Circulation*, vol. 98, pp. 839–844, 1998.
Giovanna Liuzzo, M.D. et al., "The Prognostic Value of C–Reactive Protein and Serum Amyloid A Protein in Severe Unstable Angina," *The New England Journal of Medicine*, vol. 331, No. 7, pp. 417–424, Aug. 18, 1994.
Attilio Maseri, M.D. et al., "Inflammation, Atherosclerosis, and Ishemic Events—Exploring The Hidden Side of the Moon," *The New England Journal of Medicine*, vol. 336, No. 14, pp. 1014–1015, Apr. 3, 1997.
Shi–Jen Hwang, Ph.D. et al., "Circulating Adhesion Molecules VCAM–1, ICAM–1, and E–selectin in Carotid Atherosclerosis and Incident Coronary Heart disease Cases," *Circulation*, vol. 96, pp. 4219–4225, 1997.
Haverkate F., et al., "C–reactive protein and cardiovascular disease," *Fibrinolysis & Proteolysis*, 11 (Suppl. 1), pp. 133–134, 1997 Biosis Abstract.
Di Minno G., "Platelets, Prostaglandins and Thromboses." *G. Arterioscler*, 3(2), pp. 101–109, 1979, Biosis Abstract.

*Primary Examiner*—David Saunders
*Attorney, Agent, or Firm*—Wolf, Greenfield & Sacks, PC

[57] ABSTRACT

The invention involves methods for characterizing an individual's risk profile of developing a future cardiovascular disorder by obtaining a level of the marker of systemic inflammation in the individual. The invention also involves methods for evaluating the likelihood that an individual will benefit from treatment with an agent for reducing the risk of future cardiovascular disorder.

47 Claims, 5 Drawing Sheets

SYSTEMIC INFLAMMATORY MARKERS AS DIAGNOSTIC TOOLS IN THE PREVENTION OF ATHEROSCLEROTIC DISEASES AND AS TOOLS TO AID IN THE SELECTION OF AGENTS TO BE USED FOR THE PREVENTION AND TREATMENT OF ATHEROSCLEROTIC DISEASE

RELATED APPLICATIONS

This application claims priority under Section 119 (e) of U.S. provisional applications Ser. Nos. 60/043,039 (filed Apr. 2, 1997), 60/041,950 (filed Apr. 2, 1997) and 60/070,894 (filed Jan. 9, 1998), all entitled Systemic Inflammatory Markers As Diagnostic Tools in the Prevention of Atherosclerotic Diseases And As Tools To Aid In the Selection of Agents To Be Used For The Prevention And Treatment Of Atherosclerotic Disease.

FIELD OF THE INVENTION

This invention describes the new use of a diagnostic test to determine the risk of atherosclerotic diseases such as myocardial infarction and stroke, particularly among individuals with no signs or symptoms of current disease and among nonsmokers. Further, this invention describes the new use of a diagnostic test to assist physicians in determining which individuals at risk will preferentially benefit from certain treatments designed either to prevent first or recurrent myocardial infarctions and strokes, or to treat acute and chronic cardiovascular disorders.

BACKGROUND OF THE INVENTION

Despite significant advices in therapy, cardiovascular disease remains the single most common cause of morbidity and mortality in the developed world. Thus, prevention of cardiovascular disorders such as myocardial infarction and stroke is an area of major public health importance. Currently, several risk factors for future cardiovascular disorders have been described and are in wide clinical use in the detection of individuals at high risk. Such screening tests include evaluations of total and HDL cholesterol levels. However, a large number of cardiovascular disorders occur in individuals with apparently low to moderate risk profiles, and our ability to identify such patients is limited. Moreover, accumulating data suggests that the beneficial effects of certain preventive and therapeutic treatments for patients at risk for or known to have cardiovascular disorders differs in magnitude among different patient groups. At this time, however, data describing diagnostic tests to determine whether certain therapies can be expected to be more or less effective are lacking.

Certain cardiovascular disorders, such as myocardial infarction and ischemic stroke, are associated with atherosclerosis. The mechanism of atherosclerosis is not well understood. While inflammation is hypothesized to play a role in the initiation and progression of atherosclerosis, clinical data have not established whether inflammation increases, or anti-inflammatory treatments decrease, the risk of cardiovascular disorders associated with atherosclerosis.

C-reactive protein is a marker for underlying systemic inflammation. Elevated levels of C-reactive protein have been described among patients with acute ischemia or myocardial infarction, and predict episodes of recurrent ischemia among those hospitalized with unstable angina. Further, plasma concentration of C-reactive protein is associated with risk of myocardial infarction among unhealthy patients, such as those with symptomatic angina pectoris. Plasma concentration of C-reactive protein also is associated with fatal, but not nonfatal, coronary heart disease among smokers with multiple risk factors for atherosclerosis. However, since levels of C-reactive protein increase following acute ischemia and are directly related to cigarette consumption, it has been uncertain whether statistical associations observed in these prior studies of acutely ill or high-risk populations are causal, are due to short-term inflammatory changes or are due to interrelations with other risk factors, in particular, smoking and hyperlipidemia.

SUMMARY OF THE INVENTION

This invention describes new diagnostic tests which determine and utilize the magnitude of systemic inflammation. These new tests broadly include (1) the prediction of risk of future atherosclerotic disorders such as myocardial infarction and stroke and peripheral arterial disease; and (2) the determination of the likelihood that certain individuals will benefit to a greater or lesser extent from the use of certain treatments designed to prevent and/or treat atherosclerotic disorders. These, new tests are based in part upon the following discoveries.

It has been discovered that elevated levels of markers of systemic inflammation are predictive of future cardiovascular disorders. For example, elevated levels of markers of systemic inflammation in apparently healthy, nonsmokers are predictive of an increased risk of myocardial infarction. As another example, contrary to suggestions in the prior art, elevated levels of markers of systemic inflammation in otherwise healthy smokers are predictive of an increased risk of a nonfatal myocardial infarction. As still another example, elevated levels of markers of systemic inflammation are predictive of an increased likelihood of a future stroke.

It has been discovered also that the likelihood that certain individuals will benefit to a greater or a lesser extent from the use of certain therapeutic agents for reducing the risk of a future cardiovascular disorder can be determined from the base-line level of systemic inflammation in an individual.

It further has been discovered that the predictive value of markers of systemic inflammation are independent of other predictors and, for example, are additive with risk factors derived from total cholesterol levels and total cholesterol/HDL ratios. Thus, the level of markers of systemic inflammation does not simply duplicate that which is measured when levels of cholesterol are measured.

As mentioned above, these discoveries have led to new diagnostic tests.

Thus, according to one aspect of the invention, a method is provided for evaluating the likelihood that an individual will benefit from treatment with an agent for reducing the risk of a cardiovascular disorder associated with atherosclerotic disease. The agent can be selected from the group consisting of anti-inflammatory agents, anti-thrombotic agents, anti-platelet agents, fibrinolytic agents, lipid reducing agents, direct thrombin inhibitors, and glycoprotein II b/IIIa receptor inhibitors and agents that bind to cellular adhesion molecules and inhibit the ability of white blood cells to attach to such molecules (e.g. anti-cellular adhesion molecule antibodies). (A preferred agent is aspirin). To practice the method, a level of a marker of systemic inflammation in an individual is obtained. This level then is compared to a predetermined value, wherein the level of the marker of systemic inflammation in comparison to the predetermined value is indicative of the likelihood that the individual will benefit from treatment with the agent. The individual then can be characterized in terms of the net benefit likely to be obtained by treatment with the agent.

The predetermined value can be a single value, multiple values, a single range or multiple ranges. Thus, in one embodiment, the predetermined value is a plurality of predetermined marker level ranges, and the comparing step comprises determining in which of the predetermined marker level ranges the individual's level falls. In preferred embodiments, the individual is apparently healthy. In certain embodiments, the individual also is a nonsmoker. In preferred embodiments the marker of systemic inflammation is selected from the group consisting of C-reactive protein, a cytokine and a cellular adhesion molecule. In the most preferred embodiment, the marker of systemic inflammation is C-reactive protein. Particularly useful results have been obtained with this marker.

When the marker of systemic inflammation is C-reactive protein, then a preferred predetermined value is about $1\frac{3}{4}$ mg/l of blood. Another preferred predetermined value is about 2 mg/l of blood. When ranges are employed, it is preferred that one of the plurality of ranges be below about $1\frac{3}{4}$ mg/l of blood and that another of the ranges be above about $1\frac{3}{4}$ mg/l of blood. When the marker of systemic inflammation is sICAM-1, a cellular adhesion molecule, then a preferred predetermined value is about 250 ng/ml of blood. The predetermined value will depend, of course, on the particular marker selected and even upon the characteristics of the patient population in which the individual lies, described in greater detail below.

As mentioned above, the invention is particularly adapted to determining which individuals will preferentially benefit from treatment with an agent for reducing the risk in the individuals of a cardiovascular disorder such as a future stroke or a future myocardial infarction, including nonfatal myocardial infarctions. It also permits selection of candidate populations for clinical trials and for treatment with candidate drugs, by identifying, for example, the individuals most likely to benefit from a new treatment or from a known treatment with a high risk profile of adverse side effects. Thus, the invention provides information for evaluating the likely net benefit of certain treatments for candidate patients.

According to another aspect of the invention, a method is provided for characterizing an apparently healthy, nonsmoking individual's risk profile of developing a future myocardial infarction. The method involves obtaining a level of a marker of systemic inflammation in the individual. The level of the marker then is compared to a predetermined value, and the individual's risk profile of developing a future myocardial infarction then is characterized based upon the level of the marker in comparison to the predetermined value. As in the previous aspect of the invention, the predetermined value may be a single value, a plurality of values, a single range or a plurality of ranges. In one embodiment, the predetermined value is a plurality of predetermined marker level ranges and the comparing step involves determining in which of the predetermined marker level ranges the individual's level falls. The preferred markers, predetermined values and the like are as described above.

According to still another aspect of the invention, a method is provided for characterizing an individual's risk profile of developing a future cardiovascular disorder associated with atherosclerotic disease, other than fatal myocardial infarction. A level of a marker of systemic inflammation in the individual is obtained. The level of the marker is compared to a predetermined value. The individual's risk profile of developing the future cardiovascular disorder associated with atherosclerotic disease, other than a fatal cardiovascular event, then is characterized based upon the level of the marker in comparison to the predetermined value. The predetermined value can be as described above. The individual characterized may be any individual, but preferably is an apparently healthy individual. The apparently healthy individual can be a smoker or a nonsmoker. The preferred markers and predetermined values are as described above. In one important embodiment, the cardiovascular disorder is stroke. In another important embodiment, the cardiovascular disorder is nonfatal myocardial infarction. In another important embodiment, the cardiovascular disorder is peripheral artery disease.

According to yet another aspect of the invention, a method is provided in which one uses an inflammatory marker together with a cholesterol fraction for characterizing an individual's risk profile of developing a future cardiovascular disorder associated with atherosclerotic disease. A level of a marker of systemic inflammation in the individual is obtained. The level of the marker is compared to a predetermined value to establish a first risk value. A level of a cholesterol in the individual also is obtained. The level of the cholesterol in the individual is compared to a second predetermined value to establish a second risk value. The individual's risk profile of developing the cardiovascular disorder then is characterized based upon the combination of the first risk value and the second risk value, wherein the combination of the first risk value and second risk value establishes a third risk value different from the first and second risk values. In particularly important embodiments, the third risk value is greater than either of the first and second risk values. The preferred individuals for testing, markers and predetermined values are as described above. The cardiovascular disorder can be any cardiovascular disorder associated with atherosclerotic disease, although in certain important embodiments the cardiovascular disorder is nonfatal myocardial infarction or ischemic stroke.

The invention also contemplates kits comprising a package including an assay for a marker of systemic inflammation and instructions, and optionally related materials such as number or color charts, for correlating the level of the marker as determined by the assay with a risk of developing a future cardiovascular disorder or with other patient criteria as described above. In important embodiments, the kits also include an assay for a cholesterol.

The invention also involves a method for treating subjects, with anti-inflammatory therapies, to prevent cardiovascular disorders. A non-aspirin anti-inflammatory agent is administered to a subject who has an above-normal level of a marker of systemic inflammation, but who is otherwise free of symptoms calling for an anti-inflammatory agent. The anti-inflammatory agent is administered in an amount effective to lower the risk of the subject developing a future cardiovascular disorder. The preferred subjects are apparently healthy subjects free of current need for anti-inflammatory treatment, such as free of symptoms of rheumatoid arthritis, chronic back pain, autoimmune diseases, and the like.

The invention also involves a method for treating subjects with agents that bind to cellular adhesion molecules and inhibit the ability of white blood cells to attach to such molecules, to prevent cardiovascular disorders. Such an agent is administered to a subject, preferably who has an above-normal level of a marker of systemic inflammation, but who is otherwise free of symptoms calling to such an agent. The agent is administered as an amount effective to lower the risk of the subject developing a future cardiovascular disorder. In one embodiment, the subject already has had a cardiovascular event, such as a heart attack or an angioplasty. In this embodiment, the agent can limit further injury or help prevent restenosis, post-myocardial infarction and post angioplasty, respectively. In another important embodiment, the subjects are apparently healthy subjects free of current need for anti-inflammatory treatment such as free of symptoms of rheumatoid arthritis, chronic back pain, autoimmune disease, and the like.

These and other aspects of the invention will be described in more detail below in connection with the detailed description of the invention.

DETAILED DESCRIPTION OF THE INVENTION

Figure 1:
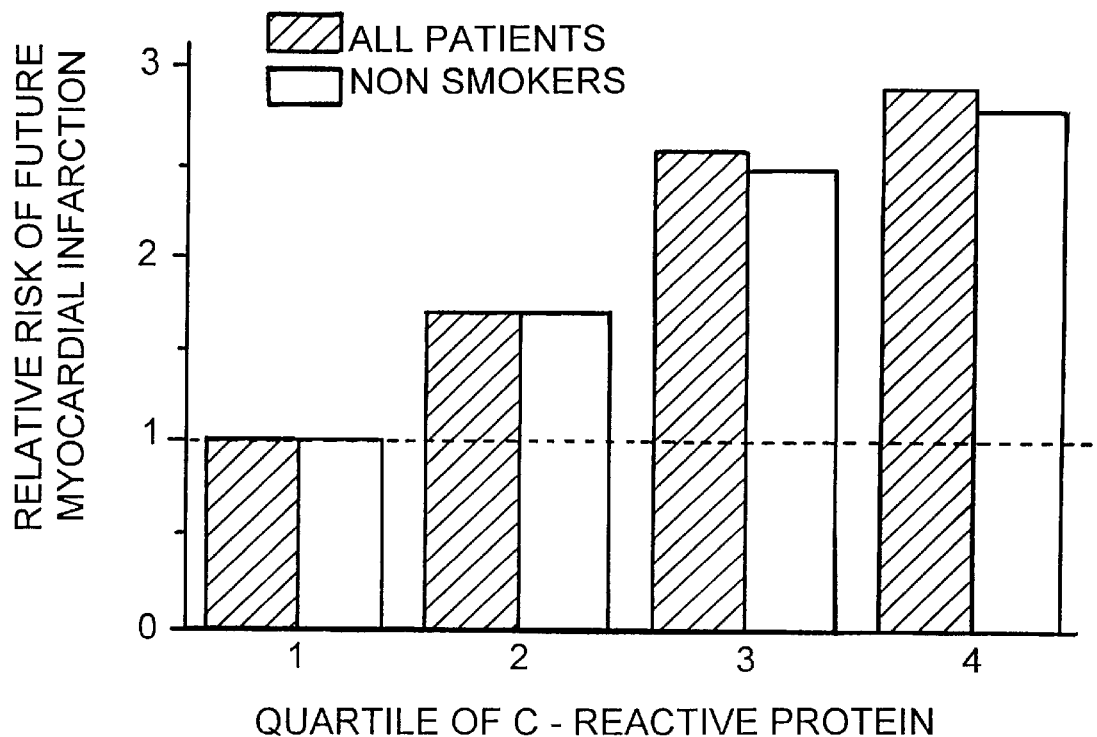
FIG. 1 is a graph demonstrating the relative risk of first myocardial infarction in the study population according to baseline level of C-reactive protein. Data are shown for all study subjects and/or non-smokers.

The primary basis for this invention is evidence from the Physicians' Health Study, a large scale, randomized, double-blind, placebo controlled trial of aspirin and beta-carotene in the primary prevention of cardiovascular disease conducted among 22,000 apparently healthy men. In that trial, baseline level of C reactive protein, a marker for underlying systemic inflammation, was found to determine the future risk of myocardial infarction and stroke, independent of a large series of lipid and non-lipid risk factors. Specifically, individuals with the highest baseline levels of C-reactive protein were found to have 3 fold increases in risk of developing future myocardial infarction and 2 fold increases in risk of developing future stroke. (FIG. 1).

Moreover, in data from the Physicians' Health Study, the risk of future myocardial infarction and stroke associated with this marker of inflammation appear to be additive to that which could otherwise be determined by usual assessment of total cholesterol and HDL cholesterol. In this trial, the predictive value of C-reactive protein was present for non-fatal as well as fatal events, was stable over long periods of time, and was present for non-smokers as well as smokers. Further, data from this trial indicate that the magnitude of benefit that apparently healthy individuals can expect from prophylactic aspirin is dependent in large part upon baseline level of C-reactive protein. In addition, these data indicate that the benefit of other therapeutic agents used in the prevention and treatment of atherosclerotic disorders may differ depending on the underlying level of C-reactive protein. These data also raised the possibility that other inflammatory markers may have an important role in determining the risk of myocardial infarction and stroke. This was tested. Data deriving from this study with regard to another marker of inflammation, plasma level of the soluble cellular adhesion molecule sICAM-1, indicate the ability of other inflammatory markers to predict atherosclerotic risk.

The current invention in one aspect describes the use of inflammatory markers to predict risk of cardiovascular disorders associated with atherosclerosis such as myocardial infarction and stroke among individuals without current evidence of disease. Thus, these data greatly extend prior observations regarding the use of inflammatory markers such as C reactive protein to predict risk among already identified high-risk populations (such as smokers) or among symptomatic ischemia patients such as those with stable and unstable angina pectoris. Indeed, since levels of C reactive protein and other acute phase reactants increase following acute ischemia and are directly related to cigarette consumption, it has been uncertain whether statistical associations observed in prior studies of acutely ill or high-risk populations are casual or due to short-term inflammatory changes, or to interrelations with other risk factors, in particular smoking and hyperlipidemia.

In marked contrast, data from the Physicians' Health Study indicate for the first time the utility of inflammatory markers to predict risk among currently healthy and otherwise low-risk individuals, to predict non-fatal as well as fatal events, to predict risk among non-smokers, and to predict risk above and beyond that associated with screening for total and HDL cholesterol. Data from the Physicians' Health Study also indicate for the first time that the efficacy of interventions designed to reduce risk of atherosclerotic events such as myocardial infarction and stroke differs in magnitude based upon a measure of the extent of underlying systemic inflammation.

The invention will be better understood with reference to the following brief explanation of terms.

"Cardiovascular disorders associated with atherosclerotic disease" includes myocardial infarction, stroke, angina pectoris and peripheral arteriovascular disease. Cardiovascular disorders associated with atherosclerotic disease do not include venous thrombosis.

"Apparently healthy", as used herein, means individuals who have not previously had an acute adverse cardiovascular event such as a myocardial infarction (i.e., individuals who are not at an elevated risk of a second adverse cardiovascular event due to a primary adverse cardiovascular event). Apparently healthy individuals also do not otherwise exhibit symptoms of disease. In other words, such individuals, if examined by a medical professional, would be characterized as healthy and free of symptoms of disease.

"Nonsmoking", as used herein, means an individual who, at the time of the evaluation, is not a smoker. This includes individuals who have never smoked as well as individuals who in the past have smoked but presently no longer smoke.

Agents for reducing the risk of a cardiovascular disorder include those selected from the group consisting of anti-inflammatory agents, anti-thrombotic agents, anti-platelet agents, fibrinolytic agents, lipid reducing agents, direct thrombin inhibitors, and glycoprotein II b/IIIa receptor inhibitors and agents that bind to cellular adhesion molecules and inhibit the ability of white blood cells to attach to such molecules (e.g. anti-cellular adhesion molecule antibodies).

Anti-inflammatory agents include Alclofenac; Alclometasone Dipropionate; Algestone Acetonide; Alpha Arnylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

Anti-thrombotic and/or fibrinolytic agents include Plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; r denotes recombinant), rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

Anti-platelet agents include Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide.

Lipid reducing agents include gemfibrozil, cholystyramine, colestipol, nicotinic acid, probucol lovastatin, fluvastatin, simvastatin, atorvastatin, pravastatin, cirivastatin.

Direct thrombin inhibitors include hirudin, hirugen, hirulog, agatroban, PPACK, thrombin aptamers.

Glycoprotein IIb/IIIa receptor Inhibitors are both antibodies and non-antibodies, and include but are not limited to ReoPro (abcixamab), lamifiban, tirofiban.

One preferred agent is aspirin.

In practicing the methods of the present invention, it is required to obtain a level of a marker of systemic inflammation in an individual. Markers of systemic inflammation are well-known to those of ordinary skill in the art. It is preferred that the markers of systemic inflammation be selected from the group consisting of C-reactive protein, cytokines, and cellular adhesion molecules. Cytokines are well-known to those of ordinary skill in the art and include human interleukins 1–17. Cellular adhesion molecules are well-known to those of ordinary skill in the art and include integrins, ICAM-1, ICAM-3, BL-CAM, LFA-2, VCAM-1, NCAM, and PECAM. The preferred adhesion molecule is soluble intercellular adhesion molecule (sICAM-1).

The level of the marker of systemic inflammation for the individual can be obtained by any art recognized method. Typically, the level is determined by measuring the level of the marker in a body fluid, for example, blood, lymph, saliva, urine and the like. The level can be determined by ELISA, or immunoassays or other conventional techniques for determining the presence of the marker. Conventional methods include sending samples of a patient's body fluid to a commercial laboratory for measurement.

The invention also involves comparing the level of marker for the individual with a predetermined value. The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as-a low-risk group, a medium-risk group and a high-risk group, or into quadrants, the lowest quadrant being individuals with the lowest risk and the highest quadrant being individuals with the highest risk.

The predetermined value can depend upon the particular population selected. For example, an apparently healthy, nonsmoker population (no detectable disease and no prior history of a cardiovascular disorder) will have a different 'normal' range of markers of systemic inflammation than will a smoking population or a population the members of which have had a prior cardiovascular disorder. Accordingly, the predetermined values selected may take into account the category in which an individual falls. Appropriate ranges and categories can be selected with no more than routine experimentation by those of ordinary skill in the art.

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies. Significantly, as is well-known in the art, only a small portion of an antibody molecule, the paratrope, is involved in the binding of the antibody to its epitope (see, in general, Clark, W. R. (1986) *The Experimental Foundations of Modem Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F9ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-know in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to cellular adhesion molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind, to the cellular adhesion molecule. This process can be repeated through several cycles of reselection of phage that bind to the cellular adhesion molecule. Repeated rounds lead to enrichment of phage bearing particular sequences. DNA sequences analysis can be conducted to identify the sequences of the expressed polypeptides. The minimal linear portion of the sequence that binds to the cellular adhesion molecule can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the cellular adhesion molecules. Thus, cellular adhesion molecules, or a fragment thereof, can be used to screen peptide libraries, including phage display libraries, to identify and select peptide binding partners of the cellular adhesion molecules.

The preferred body fluid is blood and the preferred marker is C-reactive protein. For C-reactive protein, one important-cut-off for a population of apparently healthy, nonsmokers is 1.75 mg/liter (median). Another important cut-off for C-reactive protein is 2.0 mg/liter (highest quartile of risk). In characterizing risk, numerous predetermined values can be established. In the preferred embodiment employing C-reactive protein, the cut-off values described above, and in greater detail in the example below, are surprisingly lower than those shown in the prior art where C-reactive protein levels are studied in unhealthy individuals or smokers.

There presently are commercial sources which produce reagents for assays for C-reactive protein. These include, but are not limited to, Abbott Pharmaceuticals (Abbott Park, Ill.), CalBiochem (San Diego, Calif.) and Behringwerke (Marburg, Germany). Commercial sources for inflammatory cytokine and cellular adhesion molecule measurements, include, but are not limited to, R&D Systems (Minneapolis, Minn.), Genzyme (Cambridge, Mass.) and Immunotech (Westbrook, Me.).

In preferred embodiments the invention provides novel kits or assays which are specific for, and have appropriate sensitivity with respect to, predetermined values selected on the basis of the present invention. The preferred kits, therefore, would differ from those presently commercially available, by including, for example, different cut-offs, different sensitivities at particular cut-offs as well as instructions or other printed material for characterizing risk based upon the outcome of the assay.

As discussed above the invention provides methods for evaluating the likelihood that an individual will benefit from treatment with an agent for reducing risk of a future cardiovascular disorder. This method has important implications for patient treatment and also for clinical development of new therapeutics. Physicians select therapeutic regimens for patient treatment based upon the expected net benefit to the patient. The net benefit is derived from the risk to benefit ratio. The present invention permits selection of individuals who are more likely to benefit by intervention, thereby aiding the physician in selecting a therapeutic regimen. This might include using drugs with a higher risk profile where the likelihood of expected benefit has increased. Likewise, clinical investigators desire to select for clinical trials a population with a high likelihood of obtaining a net benefit. The present invention can help clinical investigators select such individuals. It is expected that clinical investigators now will use the present invention for determining entry criteria for clinical trials.

Figure 2:
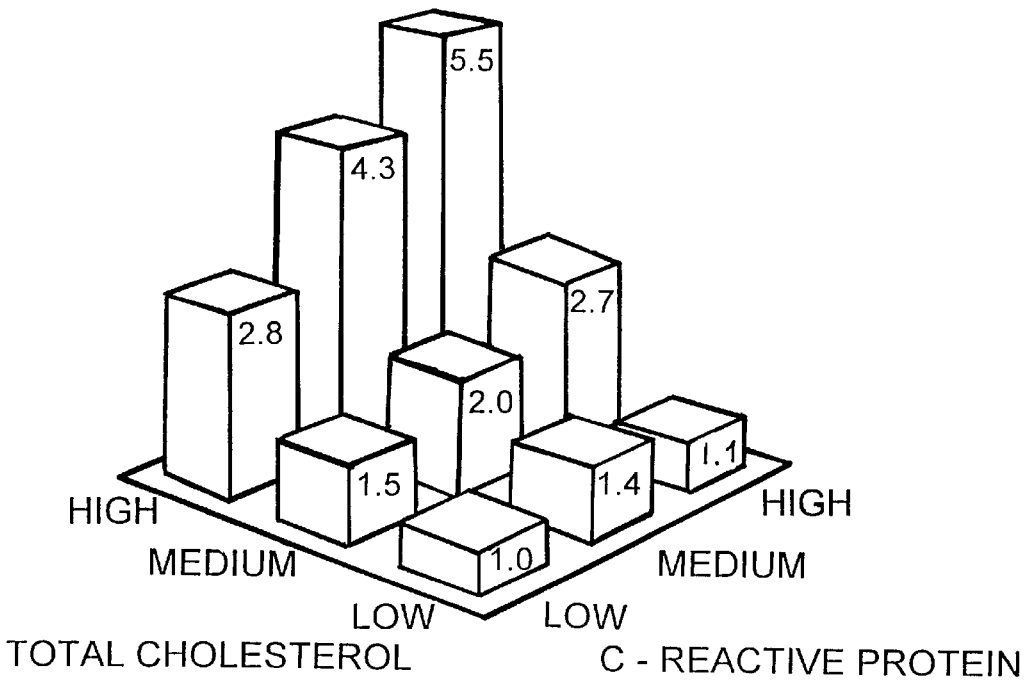
FIG. 2 is a graph demonstrating the relative risks of future myocardial infarction associated with high, middle and low tertiles of total cholesterol and C-reactive protein.
Figure 3:
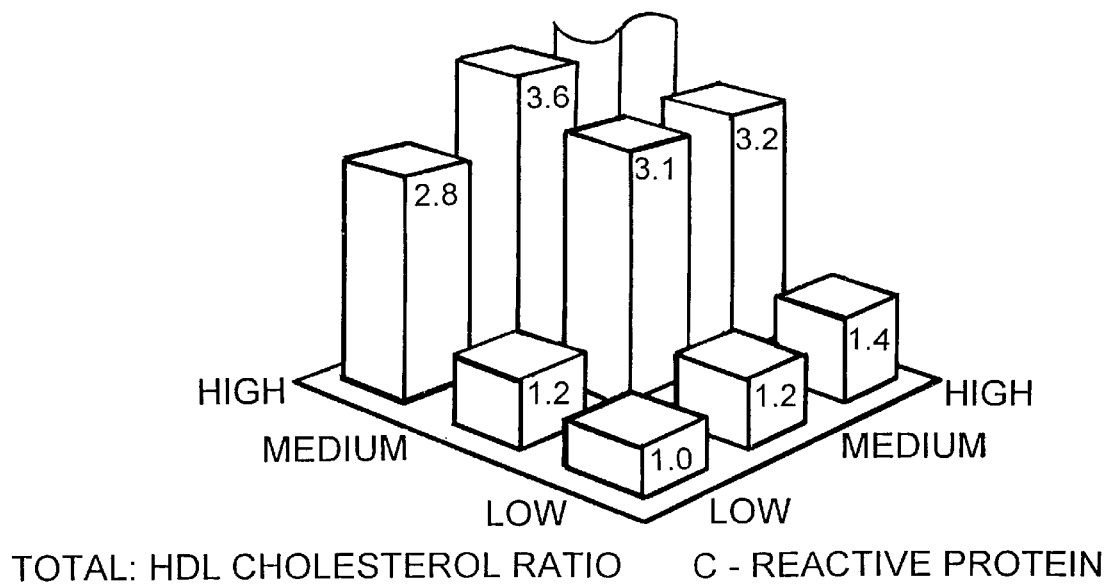
FIG. 3 is a graph demonstrating the relative risks of future myocardial infarction associated with high, middle and low tertiles of total cholesterol:HDL cholesterol ratio and C-reactive protein.

In another surprising aspect of the invention, it has been discovered that markers of systemic inflammation have predictive value independent of other known predictors of future adverse cardiovascular disorders. Thus, the present invention does not involve simply duplicating a measurement that previously could be made using other predictors. Instead, the markers of systemic inflammation are additive to prior art predictors. This is illustrated in FIGS. 2 and 3, wherein the data of the present invention is analyzed to characterize the risk profiles of individuals, taking into account, both total cholesterol levels and levels of C-reactive protein. FIG. 2 shows the relative risk of future myocardial infarction associated with high, middle and low tertiles of total cholesterol and C reactive protein. FIG. 3 shows similarly the relative risk of future myocardial infarction associated with high, middle and low tertiles of total cholesterol:HDL ratio and C reactive protein. As is abundantly clear, the risk is additive.

The invention also involves a method for treating subjects, with anti-inflammatory therapies, to prevent cardiovascular disorders. A non-aspirin anti-inflammatory agent is administered to a subject who has an above-normal level of a marker of systemic inflammation, but who is otherwise free of symptoms calling for an anti-inflammatory agent. The anti-inflammatory agent is administered in an effective amount.

An effective amount is a dosage of the anti-inflammatory agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health practioner. For example, an effective amount can depend upon the degree to which an individual has abnormally elevated levels of markers of systemic information. It should be understood that the anti-inflammatory agents of the invention are used to prevent cardiovascular disorders, that is, they are used prophylactically in subjects at risk of developing a cardiovascular disorder. Thus, an effective amount is that amount which can lower the risk of, slow or perhaps prevent altogether the development of a cardiovascular disorder. When the agent is one that binds to cellular adhesion molecules and inhibits the ability of white blood cells to attach to such molecules, then the agent may be used prophylactically or may be used in acute circumstances, for example, post-myocardial infarction or post-angioplasty. It will be recognized when the agent is used in acute circumstances, it is used to prevent one or more medically undesirable results that typically flow from such adverse events. In the case of myocardial infarction, the agent can be used to limit injury to the cardiovascular tissue which develops as a result of the myocardial infarction and in the case of restinosis the agent can be used in amounts effective to inhibit, prevent or slow the reoccurrence of blockage. In either case, it is an amount sufficient to inhibit the infiltration of white blood cells and transmigration of white blood cells into the damaged tissue, which white blood cells can result in further damage and/or complications relating to the injury.

Generally, doses of active compounds would be from about 0.01 mg/kg per day to 1000 mg/kg per day. It is expected that doses ranging from 50–500 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The anti-inflammatory agents may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the anti-inflammatory agent, which is preferably isotonic with the blood of the recipient. This aqueous preparation may be formulated according to known methods using suitable dispersing or wetting agents and suspending agents The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the anti-inflammatory agent into association with a carrier which constitutes one or more accessory ingredients. In general, the compositions are prepared by uniformly and intimately bringing the anti-inflammatory agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667, 014, 4,748,034 and 5,239,660 and (b) difusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

EXAMPLE

Study Organization

The Physicians' Health Study is a randomized, double-blind, placebo controlled, 2×2 factorial trial of aspirin and beta-carotene in the primary prevention of cardiovascular disease and cancer.

Subject Recruitment

A total of 22,071 U.S. male physicians aged 40 to 84 years in 1982 with no history of myocardial infarction, stroke, transient ischemic attack, or cancer were assigned to one of four treatment groups: 325 mg aspirin on alternate days (Bufferin, provided by Bristol-Myers), 50 mg of beta-carotene on alternate days (Lurotin, provided by BASF Corporation), both, or neither. The aspirin component of the PHS was terminated early on Jan. 25, 1988 primarily due to a statistically extreme 44 percent reduction in risk of first infarction in the aspirin group.[1] The beta-carotene component continued to scheduled termination on Dec. 31, 1995.[2]

Before randomization, between August 1982 and December 1984, potentially eligible participants were asked to provide baseline blood samples during a 16 week run-in period with all subjects given active aspirin. Blood collection kits including EDTA vacutainer tubes were sent to participants with instructions for taking blood. Participants were asked to have their blood drawn into the EDTA tubes, centrifuge the tubes, and return the plasma (accompanied by a provided cold pack) by overnight courier. Upon return, specimens were alliquotted and stored at −80° C. Of 22,071 participants in the PHS, 14,916 (68 percent) provided baseline plasma samples. Over the 14 year period of the trial, no specimen has inadvertently thawed during storage.

Endpoint Confirmation and Selection of Controls

Hospital records (and for fatal events, death certificates and necropsy reports) were requested for all reported cases of myocardial infarction, stroke, and venous thrombosis. Records were reviewed by a committee of physicians using standardized criteria to confirm or refute reported events. Endpoints reviewers were blinded to treatment assignment.

Reported myocardial infarction was confirmed if the event met World Health Organization criteria of symptoms plus either elevated enzymes or characteristic electrocardiographic changes. Silent myocardial infarctions were not included since they could not be dated accurately. Deaths due to coronary disease were confirmed based on autopsy reports, symptoms, circumstances of death, and prior history of coronary disease. Reported stroke was confirmed based on medical records showing neurological deficit of sudden or rapid onset persisting for more than 24 hours or until death. Strokes were classified as ischemic or hemorrhagic. Computed tomography was available for more than 95 percent of confirmed strokes. Reported deep venous thrombosis was confirmed by documentation of a positive venography study or a positive ultrasound study; deep venous thrombosis documented only by impedance plethysmography or Doppler examination without ultrasound were not confirmed. Reported pulmonary embolism was confirmed by positive angiogram or completed ventilation-perfusion scan demonstrating at least two segmental perfusion defects with normal ventilation.

Each participant who provided an adequate baseline plasma sample and had a confirmed myocardial infarction, stroke, or venous thrombosis after randomization was matched to one control. Controls were participating physicians who provided baseline plasma samples and reported no cardiovascular disease at the time the case reported his event. Controls were randomly selected from study participants who met the matching criteria of age (+/- one year), smoking habit (current, past, or never), and time since randomization (six month intervals). Using these methods, we evaluated 543 cases and 543 controls in this prospective nested case-control, design.

Collection of Plasma Samples and Laboratory Analysis

For each case and control, plasma collected and stored at baseline was thawed and assayed for C-reactive protein employing enzyme linked immunoabsorbant assays (ELISA) based upon purified protein and polyclonal anti-protein antibodies (Calbiochem).[3] In brief, antibodies are used to coat microtiter plate wells, and biotinylated C-reactive protein plus patient plasma is diluted 1:700 in assay buffer (phosphate-buffered saline with 0.1 percent Tween-20, and 1 percent bovine serum albumin). After competition, excess is washed off and the amount of biotinylated protein estimated by the addition of avidin-peroxidase (Vectastain, Vector Laboratories, Burlingame, Calif.). Purified proteins are then used as standards, with the protein concentrations as determined by the manufacturer. The C-reactive protein assay was standardized using the 1st International Reference Standard of the World Health Organization and has sensitivity to 0.08 ug/microliter with standard reference range between 0.5 and 2.5 mg/liter. Methods used to measure total and HDL cholesterol, triglyceride, lipoprotein(a), total plasma homocysteine, fibrinogen, D-dimer, and endogenous tissue-type plasminogen activator (tPA) antigen have been described elsewhere.[4-8]

Blood specimens were analyzed in blinded pairs with the position of the case varied at random within pairs to reduce the possibility of systematic bias and decrease interassay variability. The mean coefficient of variation for C-reactive protein across assay runs was 4.2 percent.

Statistical Analysis

Means or proportions for baseline risk factors were calculated for cases and controls. The significance of any difference in means was tested using the Student's t-test and the significance of any differences in proportions tested using the Chi square statistic. Because C-reactive protein levels are skewed, median levels were computed and the significance of any differences in median values between cases and controls assessed using Wilcoxon's Rank Sum Test. Geometric mean C-reactive protein levels were also computed after log transformation which resulted in near normal distribution. Tests for trends were used to assess any relationship of increasing levels of C-reactive protein with risks of future vascular disease after dividing the sample into quartiles defined by the distribution of the control values. Adjusted estimates were obtained using conditional logistic regression models accounting for the matching variables and controlling for randomized treatment assignment, body mass index, diabetes, history of hypertension, and a parental history of coronary artery disease. Similar models were employed to adjust for measured baseline levels of total and HDL cholesterol, triglyceride, lipoprotein(a), tPA antigen, fibrinogen, D-dimer, and homocysteine. To evaluate whether aspirin affected these relationships, analyses were repeated for all myocardial infarction events occurring on or before Jan. 25, 1988, the date of termination of randomized aspirin assignment. All P values were two-tailed and confidence intervals calculated at the 95 percent level.

Results

Table 1 shows baseline characteristics of study participants. As expected, those who subsequently developed myocardial infarction were more likely than those who remained free of vascular disease to have a history of hypertension, hyperlipidemia, or a parental history of coronary artery disease. Similarly, those who subsequently developed stroke were more likely to be hypertensive. Due to the matching, age and smoking were similar in cases and controls.

TABLE 1

Baseline Characteristics of Study Participants

| | Cardiovascular Disease During Follow-up | | | | |
|---|---|---|---|---|---|
| | None (N = 543) | Any (N = 543) | MI (N = 246) | CVA (N = 196) | DVT/PE (N = 101) |
| Age (yrs*) | 59 +/- 9.1 | 59 +/- 9.2 | 58 +/- 8.6 | 62 +/- 9.1 | 57 +/- 9.4 |
| Smoking Status (%) | | | | | |
| Never | 44 | 44 | 45 | 42 | 50 |
| Past | 41 | 41 | 40 | 40 | 44 |

TABLE 1-continued

Baseline Characteristics of Study Participants

| | Cardiovascular Disease During Follow-up | | | | |
|---|---|---|---|---|---|
| | None (N = 543) | Any (N = 543) | MI (N = 246) | CVA (N = 196) | DVT/PE (N = 101) |
| Current | 15 | 15 | 15 | 18 | 6 |
| Diabetes (%) | 4 | 7 | 5 | 12 | 2 |
| Body Mass Index (kg/m2*) | 25 +/- 2.8 | 26 +/- 3.2 | 26 +/- 3.3 | 25 +/- 3.2 | 26 +/- 2.9 |
| History of high cholesterol (%) | 9 | 13 | 17 | 10 | 7 |
| History of Hypertension (%) | 16 | 29 | 27 | 35 | 20 |
| Parental history of coronary artery disease (%) | 10 | 13 | 17 | 11 | 8 |

*values represent means +/- SD

Geometric mean and median levels of baseline C-reactive protein were significantly higher among those who subsequently developed any vascular event compared to those who did not (P<0.001). The difference between cases and controls was greatest for those who subsequently developed myocardial infarction (1.51 mg/liter vs 1.13 mg/liter, P<0.001) although differences were also significant for stroke (P=0.03), particularly those of ischemic etiology (P=0.02). In contrast, C-reactive protein levels were not significantly increased among those who subsequently developed venous thrombosis (P=0.34)(Table 2).

TABLE 2

Baseline levels of C-reactive protein among study participants who remained free of vascular disease during follow-up (controls) and among those who developed myocardial infarction, stroke, or venous thrombosis (cases)

| | Baseline Level of C-Reactive Protein (mg/liter) | | | |
|---|---|---|---|---|
| Cardiovascular Disease During Follow-up | Geometric Mean | p | Median | p |
| None (N = 543) | 1.10 | — | 1.13 | — |
| Any Vascular Event (N = 246) | 1.37 | <0.001 | 1.40 | <0.001 |
| Myocardial Infarction (N = 246) | 1.48 | <0.001 | 1.51 | <0.001 |
| Any Stroke (N = 196) | 1.30 | 0.03 | 1.36 | 0.03 |
| Ischemic Stroke (N = 154) | 1.36 | 0.01 | 1.38 | 0.02 |
| Venous Thrombosis (N = 101) | 1.24 | 0.22 | 1.26 | 0.34 |

Relative risks of developing first myocardial infarction increased significantly with each increasing quartile of baseline C-reactive protein (P for trend across quartiles<0.001) such that men in the highest quartile had risks of future myocardial infarction almost 3 times greater than those in the lowest (relative risk=2.9, 95 percent confidence interval 1.8 to 4.6, P<0.001)(Table 3). Similarly, men with the highest baseline C-reactive protein levels had twice the risk of developing future ischemic stroke (relative risk=1.9, 95 percent confidence interval 1.1 to 3.3, P=0.02). No significant associations were observed for venous thrombosis. Findings were similar in analyses limited to non-fatal events.

TABLE 3

Relative risks of future myocardial infarction, stroke, and venous thrombosis according to baseline levels of C-reactive protein.

| | Quartile of C-Reactive Protein (range, mg/liter) | | | | |
|---|---|---|---|---|---|
| | 1 ($\leq$0.55) | 2 (0.56–1.14) | 3 (1.15–2.10) | 4 ($\geq$2.11) | p-trend |
| Myocardial Infarction (total cohort) | | | | | |
| RR | 1.0 | 1.7 | 2.6 | 2.9 | <0.001 |
| 95% CI | — | 1.1–2.9 | 1.6–4.3 | 1.8–4.6 | |
| p | — | 0.03 | <0.001 | <0.001 | |
| Myocardial Infarction (non-smokers) | | | | | |
| RR | 1.0 | 1.7 | 2.5 | 2.8 | <0.001 |
| 95% CI | — | 1.0–2.8 | 1.5–4.1 | 1.7–4.7 | |
| p | — | 0.06 | <0.001 | <0.001 | |
| Ischemic Stroke | | | | | |
| RR | 1.0 | 1.7 | 1.9 | 1.9 | 0.03 |
| 95% CI | — | 0.9–2.9 | 1.1–3.2 | 1.1–3.3 | |
| p | — | 0.07 | 0.02 | 0.02 | |
| Venous Thrombosis | | | | | |
| RR | 1.0 | 1.1 | 1.2 | 1.3 | 0.38 |
| 95% CI | — | 0.6–2.0 | 0.7–2.3 | 0.7–2.4 | |
| p | — | 0.78 | 0.51 | 0.42 | |

95% CI = 95 percent confidence interval

Figure 4:
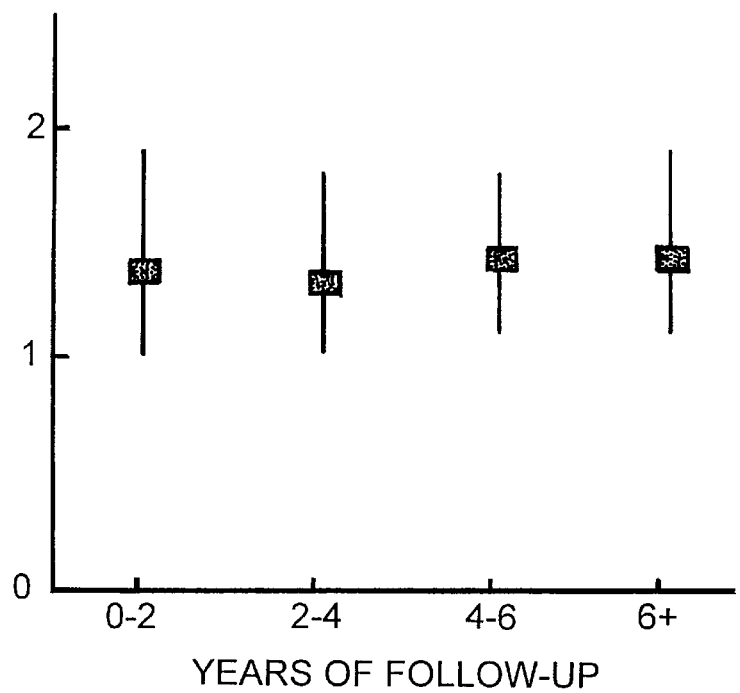
FIG. 4 is a graph demonstrating relative risks (and 95 percent confidence interval) of first myocardial infarction associated with each increasing quartile of baseline C-reactive protein, according to year of study follow-up.

To evaluate whether increased baseline levels of C-reactive protein were associated with early rather than late thrombosis, we stratified the analysis of myocardial infarction by years of follow-up. The relative risk of future myocardial infarction associated with the highest quartile of C-reactive protein (as compared to the lowest quartile) ranged between 2.4 for events occurring in the first two years of follow-up to 3.2 for events occurring 6 or more years into study follow-up (Table 4). Similarly, the relative risk of future myocardial infarction associated with a one quartile change in C-reactive protein was stable over long time periods (FIG. 4).

TABLE 4

Relative risks of first myocardial infarction associated with the highest quartile of baseline C-reactive protein compared to the lowest quartile, according to year of study follow-up.

| | Follow-Up Time (years) | | | |
|---|---|---|---|---|
| | 0–2 | 2–4 | 4–6 | 6+ |
| Total Cohort | | | | |
| RR | 2.4 | 2.9 | 2.8 | 3.2 |
| 95% CI | 0.9–6.8 | 1.1–7.6 | 1.1–6.9 | 1.2–8.5 |
| p | 0.09 | 0.03 | 0.03 | 0.02 |
| Non-Smokers | | | | |
| RR | 2.8 | 2.9 | 2.7 | 2.9 |
| 95% CI | 0.9–8.7 | 1.0–8.3 | 1.0–7.0 | 1.1–8.2 |
| p | 0.07 | 0.05 | 0.05 | 0.04 |

95% CI = 95 percent confidence interval

Smokers had significantly higher median levels of C-reactive protein than non-smokers (2.20 mg/liter vs 1.19 mg/liter, P<0.001). Because of the match by smoking status, we minimized the potential for confounding by smoking. However, to assess for effect modification, we repeated analyses limiting the cohort to non-smokers. As also shown in Table 3, the relative risks of future myocardial infarction among non-smokers significantly increased with each increasing quartile of C-reactive protein (P-trend<0.001). Similarly, the long term effects of C-reactive protein on risk of myocardial infarction were virtually identical among non-smokers (Table 4).

The relationship between C-reactive protein and myocardial infarction was not significantly altered in analyses which adjusted for body mass index, diabetes, hypertension, a family history of premature coronary artery disease, total cholesterol, HDL cholesterol, triglycerides, lipoprotein(a), tPA antigen, D-dimer, fibrinogen, or homocysteine (Table 5).

TABLE 5

Relative risks* of future myocardial infarction according to baseline levels of C-reactive protein, adjusted for lipid and non-lipid variables.

| | Quartile of C-Reactive Protein (range, mg/liter) | | | | |
|---|---|---|---|---|---|
| Variable(s) Adjusted for: | 1 ($\leq$0.55) | 2 (0.56–1.14) | 3 (1.15–2.10) | 4 ($\geq$2.11) | p-trend |
| Total and HDL Cholesterol | | | | | |
| Adjusted RR | 1.0 | 1.8 | 2.2 | 2.3 | 0.002 |
| 95% CI | — | 1.0–3.1 | 1.3–3.7 | 1.4–3.9 | |
| p | — | 0.05 | 0.004 | 0.002 | |
| Triglyceride Level | | | | | |
| Adjusted RR | 1.0 | 1.8 | 2.1 | 2.8 | <0.001 |
| 95% CI | — | 1.0–3.2 | 1.2–3.7 | 1.6–4.9 | |
| p | — | 0.06 | 0.008 | <0.001 | |
| Lipoprotein(a) | | | | | |
| Adjusted RR | 1.0 | 2.0 | 2.5 | 2.5 | <0.001 |
| 95% CI | — | 1.2–3.4 | 1.5–4.2 | 1.5–4.2 | |
| p | — | 0.01 | <0.001 | <0.001 | |
| tPA antigen level | | | | | |
| Adjusted RR | 1.0 | 1.7 | 1.9 | 2.9 | 0.002 |
| 95% CI | — | 0.9–3.4 | 1.0–3.6 | 1.5–5.6 | |
| p | — | 0.13 | 0.06 | 0.002 | |
| total plasma homocysteine level | | | | | |
| Adjusted RR | 1.0 | 1.8 | 2.9 | 3.6 | <0.001 |
| 95% CI | — | 1.1–3.1 | 1.7–4.8 | 2.1–5.9 | |
| p | — | 0.02 | <0.001 | <0.001 | |
| D-dimer level | | | | | |
| Adjusted RR | 1.0 | 2.2 | 2.4 | 2.7 | 0.001 |
| 95% CI | — | 1.2–4.1 | 1.3–4.2 | 1.5–4.7 | |
| p | — | 0.007 | 0.003 | <0.001 | |
| fibrinogen level | | | | | |
| Adjusted RR | 1.0 | 2.2 | 2.2 | 2.9 | 0.01 |
| 95% CI | — | 1.1–4.7 | 1.0–4.4 | 1.4–5.9 | |
| p | — | 0.04 | 0.04 | 0.005 | |
| Body mass index (kg/m$^2$), diabetes, history of hypertension, and family history of premature CAD | | | | | |
| Adjusted RR | 1.0 | 1.5 | 2.4 | 2.6 | <0.001 |
| 95% CI | — | 0.9–2.5 | 1.5–4.0 | 1.6–4.4 | |
| p | — | 0.14 | <0.001 | <0.001 | |

*All models further adjusted for randomized aspirin and beta-carotene assignment.
RR = relative risk, 95% CI = 95 percent confidence intervals To assess whether the beneficial effect of aspirin on myocardial infarction varied according to baseline C-reactive protein level, we repeated these analyses for events occurring prior to Jan. 25, 1988, the date of termination of the randomized aspirin treatment.

Figure 5:
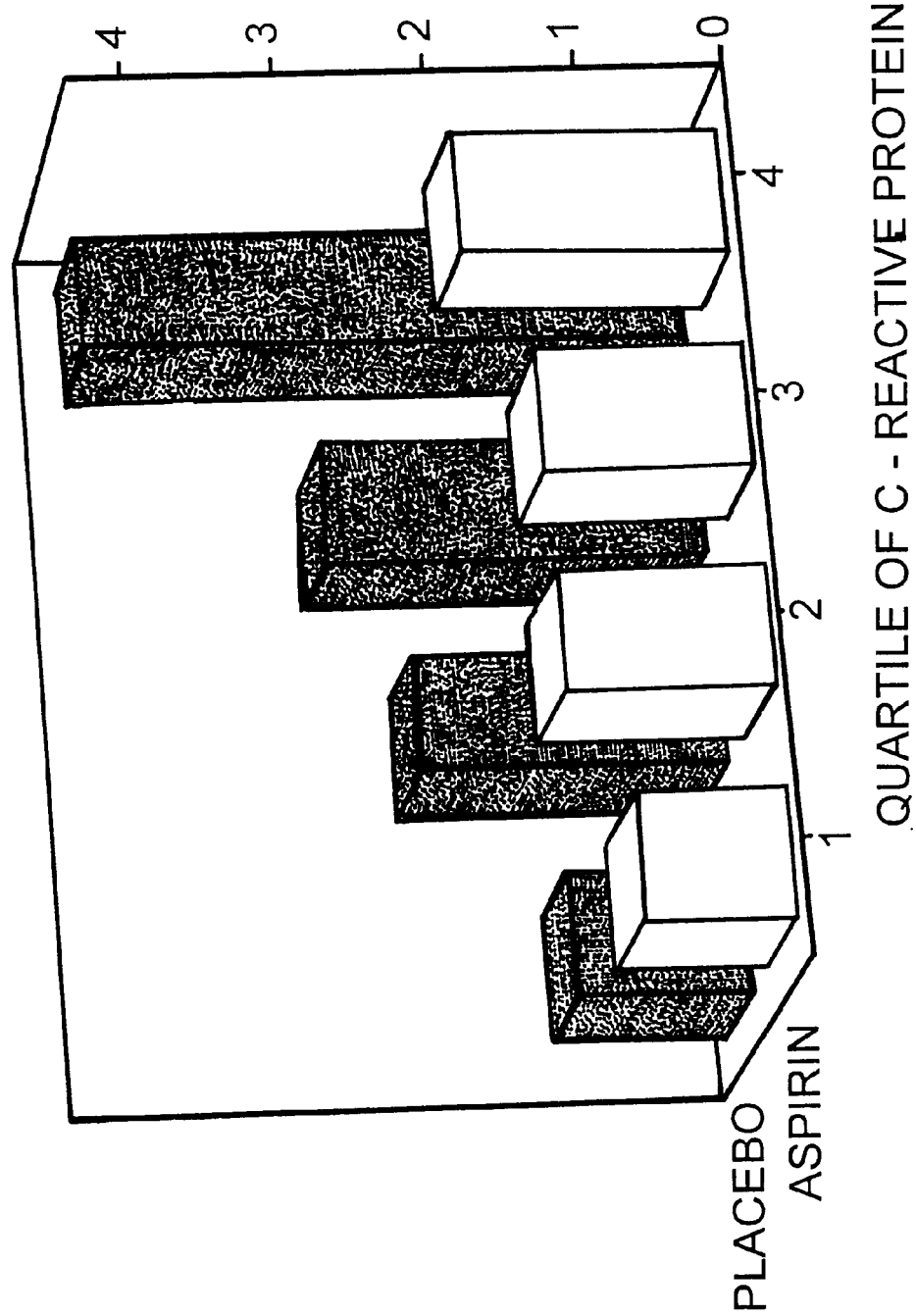
FIG. 5 is a graph demonstrating relative risks of first myocardial infarction associated with baseline levels of C-reactive protein, stratified by randomized assignment to aspirin or placebo therapy. Analyses are limited to events occurring prior to unblinding of the aspirin component of the Physicians' Health Study. The reduction in risk of myocardial infarction associated with aspirin use was 13.9 percent in the first (lowest) quartile of C-reactive protein, 33.4 percent in the second quartile, 46.3 percent in the third quartile, and 55.7 percent in the fourth (highest) quartile.

Risks of developing future myocardial infarction increased with each increasing quartile of C-reactive protein for men randomly assigned to either aspirin or placebo, and rates of myocardial infarction were lower in the aspirin group for all quartiles of C-reactive protein (FIG. 5). However, the magnitude of the beneficial effect of aspirin on preventing myocardial infarction was directly related to baseline C-reactive protein level. Specifically, randomized aspirin assignment was associated with a large and statistically significant reduction in risk of myocardial infarction among men with baseline C-reactive protein levels in the highest quartile (risk reduction=55.7 percent, P=0.02). However, among those with baseline C-reactive protein levels in the lowest quartile, the reduction in risk associated with aspirin was far smaller and no longer statistically significant (risk reduction=13.9 percent, P=0.77). These effects were linear across quartiles such that the apparent benefit of aspirin diminished in magnitude with each decreasing quartile of inflammatory risk (FIG. 5). This finding remained essentially unchanged after further adjustment for other coronary risk factors and the interaction between assignment to the aspirin group and baseline C-reactive protein level (treated as a log transformed continuous variable) was statistically significant (P=0.048).

Data from the Physicians Health Study also indicate that measures of inflammation such as C-RP predict the future risk of developing peripheral arterial disease, another clinical manifestation of systemic atherosclerosis. For example, those with baseline levels of C-RP in excess of 2.0 mg/liter had twice the risk of developing future peripheral arterial disease as did those with lower levels. Moreover, in these data, the risks of developing peripheral arterial disease severe enough to require surgical intervention was increased fourfold for those with the highest baseline levels of C-RP.

To evaluate whether C-reactive protein might be a predictor of risk over and above that associated with cholesterol levels, a series of stratified analyses were further performed. In this regard, C-reactive protein was found to predict risk of future myocardial infarction among those with low as well as high levels of total cholesterol, and among those with low as well as high total cholesterol to HDL cholesterol ratios. Finally, to investigate whether the effect of C-reactive protein are addictive to that of cholesterol, we performed further analyses in which study subjects were characterized by tertile (low, middle, or high) of cholesterol as well as C-reactive protein. Similar analyses were performed in which study subject were characterized by tertile of the total cholesterol to HDL cholesterol ratio. As shown in FIGS. 2 and 3, the risks of myocardial infarction associate with C-reactive protein appear addictive to that of lipid parameter alone.

Figure 6:
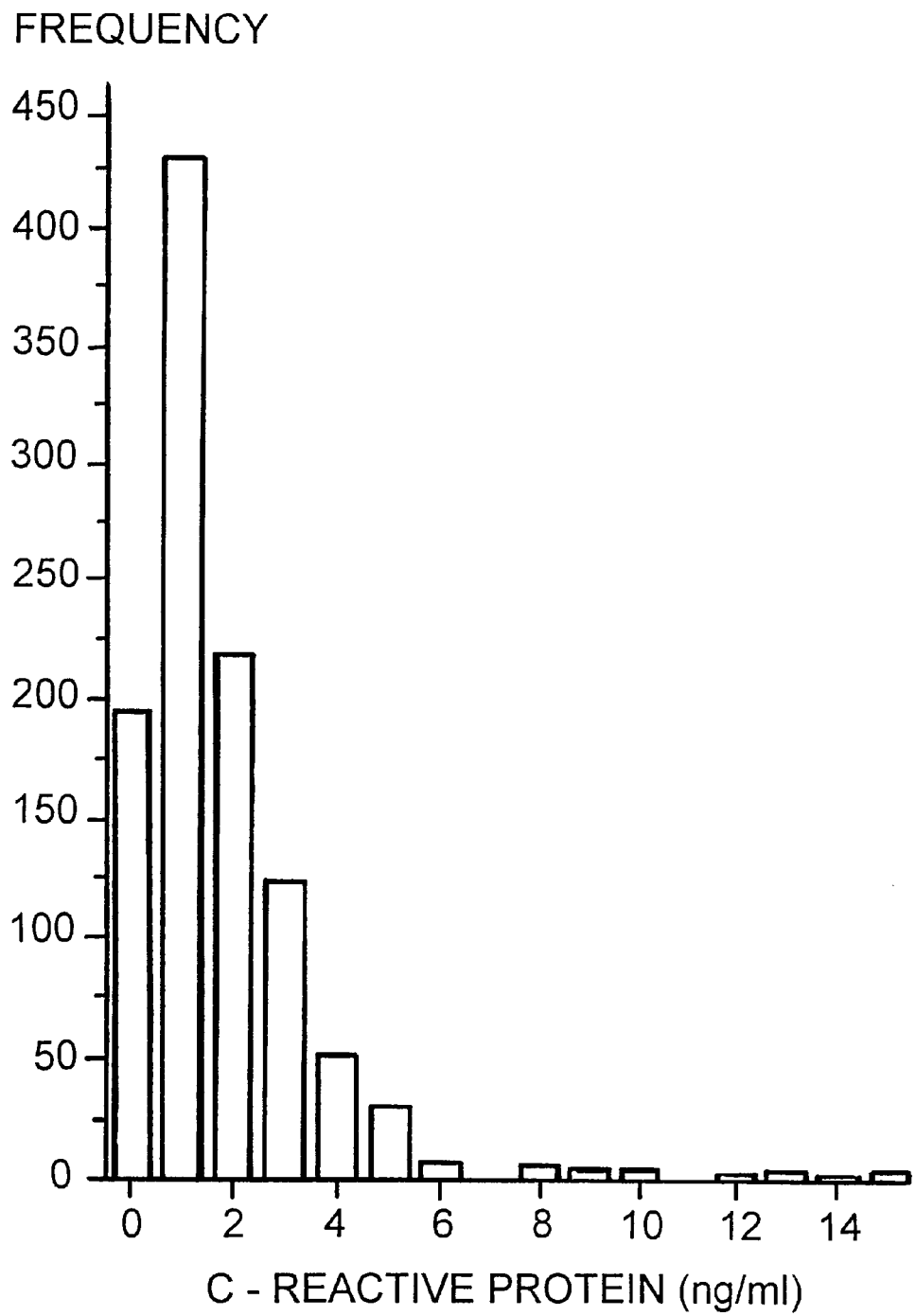
FIG. 6 is a graph demonstrating the distribution of levels of C-reactive protein in the population studied in Example. 1.
Figure 7:
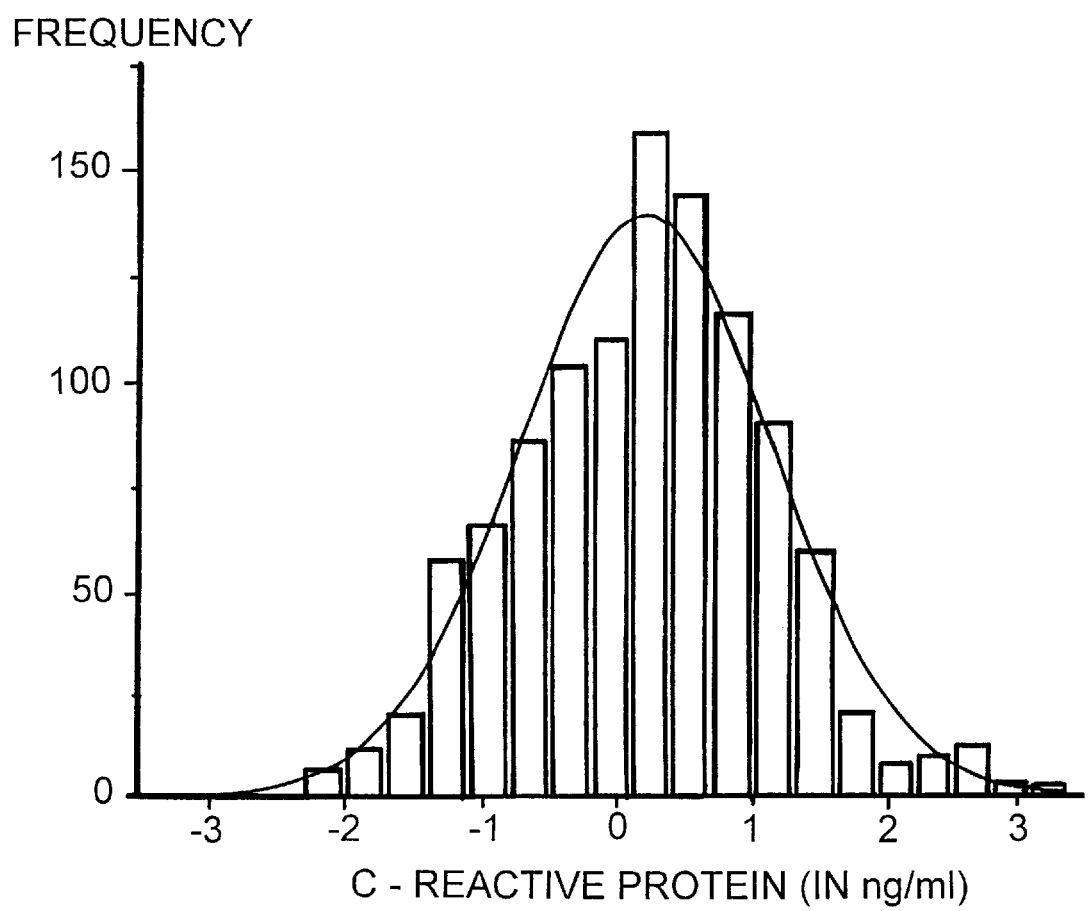
FIG. 7 is a graph demonstrating the normal bell curve distribution which occurs when the C-reactive protein levels of FIG. 5 are log normalized.

The actual C-reactive protein levels for the tested population are shown graphically in FIG. 6. The log normalized C-reactive protein levels are shown in FIG. 7, which demonstrates clearly the normal bell curve distribution in our population. The mean C-reactive protein was 1.75 and the standard deviation was 2.2. The mean of the log C-reactive protein was about 0.1 and the standard deviation was about 1. The relative ability to produce future cardiovascular disorder of another marker of systemic inflammation, soluble intracellular adhesion molecule (sICAM-1), also was evaluated. Table 6 shows the relative risks (RR) of future myocardial infarction according to baseline levels of s-ICAM-1. A statistically significant association was observed. The relationship between s-ICAM and myocardial infarction also is not significantly altered in analysis which adjusted for body mass index, diabetes, a family history of premature coronary artery disease, hyperlipidemia, and a history of hypertension.

TABLE 6

Relative risks (RR) of future myocardial infarction according to baseline levels of soluble intercellular adhesion molecule (sICAM-1)

| | Quartile of sICAM-1 (range, ng/liter) | | | | |
|---|---|---|---|---|---|
| | 1 ($\leq$193) | 2 (193–224) | 3 (225–259) | 4 (>259) | p-trend |
| Crude RR | 1.0 | 0.8 | 1.0 | 1.5 | 0.01 |
| Lipid Adjusted* RR | 1.0 | 0.7 | 0.9 | 1.5 | 0.01 |
| Fully Adjusted** RR | 1.0 | 1.1 | 1.0 | 1.9 | 0.01 |

*Matched for smoking and age, controlled for total and HDL cholesterol
**Matched for smoking and age, controlled for history of hypertension, hyperlipidemia, body mass index, diabetes, and a family history of premature CAD
95% CI = 95 percent confidence interval Discussion These prospective data indicate that baseline C-reactive protein level among apparently healthy men predicts risk of first myocardial infarction and ischemic stroke. Further, the risks of arterial thrombosis associated with C-reactive protein were stable over long periods of time and were not modified by other factors including smoking, body mass index, blood pressure, total and HDL cholesterol, triglyceride, lipoprotein(a), tPA antigen, D-dimer, fibrinogen, or homocysteine. In these data, the risk of future myocardial infarction associated with C-reactive protein appears to be addictive to that associated with either total cholesterol or the total cholesterol to HDL cholesterol ratio. In contrast, the benefit of aspirin in reducing risk of first myocardial infarction diminished significantly with decreasing C-reactive protein level, an intriguing finding as this agent has anti-inflammatory as well as anti-platelet properties. Finally, there was no significant association for venous thromboembolism suggesting that the relationship of inflammation with vascular risk may be limited to the arterial circulation. We also observed a significant association between risk of future myocardial infarction and a second measure of systemic inflammation, sICAM-1.

Since blood samples were collected at baseline, we can exclude the possibility that acute ischemia affected C-reactive protein levels. Further, the statistically significant associations observed were present among non-smokers indicating that the effect of C-reactive protein on vascular risk is not simply the result of cigarette consumption.[9,10] Thus, our prospective data relating baseline C-reactive protein level to future risks of myocardial infarction and stroke among apparently healthy men greatly extends prior observations from studies of acutely ill patients[12], patients with symptomatic coronary disease[11], or those at high risk due primarily to cigarette consumption.[9] Moreover, in these data, the effects of C-reactive protein were independent of a large number of lipid and non-lipid risk factors.

The mechanisms by which C-reactive protein is related to atherothrombosis are uncertain. Prior infection with *Chlamydia pnuemoniae, Heliobacter pylori, Herpes simplex* virus, or cytomegalovirus may be a source of the chronic inflammation detected by C-reactive protein.[13-19] It is also possible that C-reactive protein is a surrogate for interleukin-6[20], a cellular cytokine associated with macrophage and monocyte recruitment into atherosclerotic plaque.[21] In addition, C-reactive protein can induce monocytes to express tissue-factor, a membrane glycoprotein important in the initiation of coagulation.[22] Finally, it had been hypothesized that bronchial inflammation secondary to smoking is responsible for associations seen in prior studies relating C-reactive protein to vascular risk.[9] In this regard, our observation that the effect of C-reactive protein is present among non-smokers makes bronchial inflammation a less likely mechanism. Further, the finding that the effects of C-reactive protein are stable over long time periods suggests that acute effects on clotting are unlikely.

Our data regarding the interrelation of C-reactive protein and aspirin merit careful consideration. In the Physicians' Health Study, aspirin reduced risks of first myocardial infarction by 44 percent.[1] The present findings indicate that the effect of aspirin on first myocardial infarction was greatest among those with highest baseline C-reactive protein levels and that the benefit diminished significantly in magnitude with decreasing concentration of this inflammatory marker.

Some conclusions may be drawn. First, among apparently healthy men, baseline level of inflammation as assessed by C-reactive protein predicts risk of first myocardial infarction and ischemic stroke, independent of other risk factors. Second, baseline C-reactive protein level is not associated with venous thrombosis, a vascular event generally not associated with atherosclerosis. Third, C-reactive protein is not simply a short term marker as previously demonstrated for patients with unstable angina[12], but also a long term marker of risk, even for events occurring after 6 or more years. This observation suggests that the effects of inflammation are likely mediated through a chronic, process, and excludes the possibility that undetected acute illness at baseline is responsible for observed effects. Fourth, these data suggest that assessment of C-reactive protein can add to our ability to predict atherosclerotic risk, over and above that defined by levels of total cholesterol and the total cholesterol to HDL cholesterol ratio. Finally, the benefits of aspirin appear to be modified by underlying inflammation.

1. Steering Committee of the Physicians' Health Study Research Group. Final report of the aspirin component of the ongoing Physicians' Health Study. N Engl J Med 1989;321:129–35.
2. Hennekens C H, Buring J E, Manson J E, et al. Lack of effect of long-term supplementation with beta carotene on the incidence of malignant neoplasms and cardiovascular disease. N Engl J Med 1996;334:1145–9.
3. Macy E M, Hayes T E, Tracy R P. Variability in the measurement of C-reactive protein in healthy adults: implications for reference interval and epidemiologic methods. Clin Chem 1997; 43–52–58.
4. Stampfer M J, Sacks F M, Salvini S, Willett W C, Hennekens C H. A prospective study of cholesterol, apolipoproteins, and the risk of myocardial infarction. N Engl J Med 1991;325:373–81.
5. Ridker P M, Hennekens C H, Stampfer M J. A prospective study of lipoprotein(a) and the risk of myocardial infarction. JAMA 1993;270:2195–2199.
6. Ridker P M, Hennekens C H, Selhub J, Miletich J P, Malinow M R, Stampfer M J. Interrelation of hyperhomocyst(e)inemia, factor V Leiden, and risks of future venous thromboembolism. Circulation 1997 Apr. 1, 1995 (7) 1777–82.
7. Ridker P M, Vaughan D E, Stampfer M J, Manson J E, Hennekens C H. Endogenous tissue-type plasminogen activator and risk of myocardial infarction. Lancet 1993; 341:1165–1168.
8. Ridker P M, Hennekens C H, Cerskus A, Stampfer M J. Plasma concentration of cross-linked fibrin degradation product (d-Dimer) and the risk of future myocardial infarction among apparently healthy men. Circulation 1994;90:2236–2240.
9. Kuller L H, Tracy R P, Shaten J, Meilahn E N, for the MRFIT Research Group. Relationship of C-reactive protein and coronary heart disease in the MRFIT nested case-control study. Am J Epidimiology 1996;144:537–47.
10. Das I. Raised C-reactive protein levels in serum from smokers. Clinica Chimica Acta 1985;153:9–13.
11. Thompson S G, Kienast J, Pyke S D M, Haverkate F, van de Loo J C W, for the European Concerted Action on Thrombosis and Disabilities Angina Pectoris Study Group. Hemostatic factors and the risk of myocardial infarction or sudden death in patients with angina pectoris. N Engl J Med 1995;332:635–41.
12. Liuzzo G, Biasucci L M, Gallimore J R, et al. The prognostic value of C-reactive protein and serum amyloid A protein in severe unstable angina. N Engl J Med 1994;331:417–24.
13. Buja L M. Does atherosclerosis have an infectious etiology? Circulation 1996; 94:872–873.
14. Grayston J T. Chlamydia in atherosclerosis. Circulation 1993;87:1408–1409.
15. Saikku P, Leinonen M, Tenkanen L, et al. Chronic *Chlamydia pneumoniae* infection as a risk factor for coronary heart disease in the Helsinki Heart Study. Ann Intern Med 1992;1 16:273–278.
16. Thom D H, Grayston J T, Siscovick D S, Wang S-P, Weiss N S, Daling J R. Association of prior infection with chlarnydia pneumoniae and angiographically demonstrated coronary artery disease. JAMA 1992;268:68–72.
17. Melnick J L, Adam E, DeBakey M E. Possible role of cytomegalovirus in atherogenesis. JAMA 1990;263;2204–7.
18. Mendall M A, Goggin P M, Molineaux N, et al. Relation of *Helicobacter pylori* infection and coronary heart disease. Br Heart J 1994;71;437–9.
19. Patel P, Mendall M A, Carrington D, et al. Association of *Helicobacter pylori* and *Chlamydia pneumoniae* infections with coronary heart disease and cardiovascular risk factors. Br Med J 1995;311:711–4.
20. Bataille R, Klein B. C-reactive protein levels as a direct indicator of interleukin-6 levels in humans in vivo. Arthritis and Rheumatism 1992;35:982–984.
21. Biasucci L M, Vitelli A, Liuzzo G, et al. Elevated levels of interleukin-6 in unstable angina. Circulation 1996;94:874–877.
22. Cermak J, Key N S, Bach R R, et al. C-reactive protein induces human peripheral blood monocytes to synthesize tissue factor. Blood 1993;82:513–20.

We claim:

1. A method for characterizing an apparently healthy, nonsmoking individual's risk profile of developing a future myocardial infarction, comprising obtaining a level of a marker of systemic inflammation in the individual,
   comparing the level of the marker to a predetermined value, and
   characterizing the individual's risk profile of developing a future myocardial infarction based upon the level of the marker in comparison to the predetermined value.

2. The method of claim 1, wherein the predetermined value is a plurality of predetermined marker level ranges and said comparing step comprises determining in which of said predetermined marker level ranges said individuals level falls.

3. The method of claim 1, wherein the marker of systemic inflammation is selected from the group consisting of C-reactive protein, a cytokine and a cellular adhesion molecule.

4. The method of claim 1, wherein the marker of systemic inflammation is C-reactive protein.

5. The method of claim 4, wherein the predetermined value is about 1¾ mg/l of blood or higher.

6. The method of claim 4, wherein the predetermined value is about 2.0 mg/l of blood.

7. The method of claim 4, wherein the predetermined marker level is a plurality of predetermined marker level ranges, one of said plurality being below about 1.75 mg/l blood and another of said ranges being about 1.75 mg/l blood, and wherein said comparing step comprises determining in which of said plurality of predetermined marker level ranges said individual's level falls.

8. The method of claim 1, wherein the marker of systemic inflammation is soluble intercellular adhesion molecule (sICAM-1).

9. The method of claim 8, wherein the predetermined value is about 250 ng/ml of blood or higher.

10. A method for characterizing an individual's risk profile of developing a future cardiovascular disorder associated with atherosclerotic disease, other than fatal myocardial infarction, comprising
    obtaining a level of a marker of systemic inflammation in the individual,
    comparing the level of the marker to a predetermined value, and characterizing the individual's risk profile of developing said future cardiovascular disorder associated with atherosclerotic diseases other than fatal myocardial infarction, based upon the level of the marker in comparison to the predetermined level.

11. The method of claim 10, wherein the predetermined value is a plurality of predetermined marker level ranges and said comparing step comprises determining in which of said predetermined marker level ranges said individuals level falls.

12. The method of claim 10, wherein said individual is an apparently healthy, non-smoking individual.

13. The method of claim 10, wherein the marker of systemic inflammation is selected from the group consisting of C-reactive protein, a cytokine and a cellular adhesion molecule.

14. The method of claim 10, wherein the marker of systemic inflammation is C-reactive protein.

15. The method of claim 14, wherein the predetermined value is about 1¾ mg/l of blood.

16. The method of claim 14, wherein the predetermined value is about 2.0 mg/l of blood.

17. The method of claim 14, wherein the predetermined marker level is a plurality of predetermined marker level ranges, one of said plurality being below about 1.75 mg/l blood and another of said ranges being about 1.75 mg/l blood, and wherein said comparing step comprises determining in which of said plurality of predetermined marker level ranges said individual's level falls.

18. The method of claim 10, wherein the marker of systemic inflammation is soluble intercellular adhesion molecule (sICAM-1).

19. The method of claim 18, wherein the predetermined value is about 250 ng/ml of blood or higher.

20. The method of any one of claim 10–19, wherein the cardiovascular disorder is stroke.

21. The method of any one of claims 10–19, wherein the cardiovascular disorder is nonfatal myocardial infarction.

22. A method for characterizing an individual's risk profile of developing a future cardiovascular disorder associated with atherosclerotic disease, comprising obtaining a level of a marker of systemic inflammation in the individual, comparing the level of the marker to a first predetermined value to establish a first risk value, obtaining a level of a cholesterol in the individual, comparing the level of the cholesterol to a second predetermined value to establish a second risk value, and characterizing the individual's risk profile of developing the cardiovascular disorder based upon the combination of the first risk value and the second risk value, wherein the combination of the first risk value and second risk value establishes a third risk value different from said first and second risk values.

23. The method of claim 22, wherein the first predetermined value is a first plurality of predetermined marker level ranges and said comparing step comprises determining in which of said predetermined marker level ranges said individuals level falls.

24. The method of claim 22, wherein said individual is an apparently healthy, non-smoking individual.

25. The method of claim 22, wherein the marker of systemic inflammation is selected from the group consisting of C-reactive protein, a cytokine and a cellular adhesion molecule.

26. The method of claim 22, wherein the marker of systemic inflammation is C-reactive protein.

27. The method of claim 26, wherein the first predetermined value is about 1¾ mg/l of blood.

28. The method of claim 26, wherein the first predetermined value is about 2.0 mg/l of blood.

29. The method of claim 26, wherein the first predetermined marker level is a plurality of predetermined marker level ranges, one of said plurality being below about 1.75 mg/l blood and another of said ranges being about 1.75 mg/l blood, and wherein said comparing step comprises determining in which of said plurality of predetermined marker level ranges said individual's level falls.

30. The method of claim 22, wherein the marker of systemic inflammation is soluble intercellular adhesion molecule (sICAM-1).

31. The method of claim 30, wherein the first predetermined value is about 250 ng/ml of blood or higher.

32. The method of any one of claims 22–31, wherein the cardiovascular disorder is stroke.

33. The method of any one of claims 22–31, wherein the cardiovascular disorder is nonfatal myocardial infarction.

34. The method of any one of claims 22–31, wherein the third risk value is greater than either of the first and second risk values.

35. A method for evaluating the likelihood that an individual will benefit from treatment with an agent for reducing the risk of an cardiovascular disorder associated with atherosclerotic disease, the agent selected from the group consisting of anti-inflammatory agents, anti-thrombotic agents, anti-platelet agents, fibrinolytic agents, lipid reducing agents, direct thrombin inhibitors, and glycoprotein II b/IIIa receptor inhibitors comprising:

obtaining a level of a marker of systemic inflammation in the individual, and comparing the level of the marker to a predetermined value, wherein the level of the marker of systemic inflammation in comparison to the predetermined value is indicative of whether the individual will benefit from treatment with said agents.

36. The method of claim 35, wherein the predetermined value is a plurality of predetermined marker level ranges and said comparing step comprises determining in which of said predetermined marker level ranges said individuals level falls.

37. The method of claim 35, wherein said individual is an apparently healthy, non-smoking individual.

38. The method of claim 35, wherein the marker of systemic inflammation is selected from the group consisting of C-reactive protein, a cytokine and a cellular adhesion molecule.

39. The method of claim 35, wherein the marker of systemic inflammation is C-reactive protein.

40. The method of claim 39, wherein the predetermined value is about 1¾ mg/l of blood or higher.

41. The method of claim 39, wherein the predetermined value is about 2.0 mg/l of blood or higher.

42. The method of claim 39, wherein the predetermined marker level is a plurality of predetermined marker level ranges, one of said plurality being below about 1.75 mg/l blood and another of said ranges being about 1.75 mg/l blood, and wherein said comparing step comprises determining in which of said plurality of predetermined marker level ranges said individual's level falls.

43. The method of claim 35, wherein the marker of systemic inflammation is soluble intercellular adhesion molecule (sICAM-1).

44. The method of claim 43, wherein the predetermined value is about 250 ng/ml blood or higher.

45. The method of any one of claims 35–44, wherein the cardiovascular disorder is stroke.

46. The method of any one of claims 35–44, wherein the cardiovascular disorder is myocardial infarction.

47. The method of any one of claims 35–44, wherein the agent is aspirin.

* * * * *

UNITED STATES PATENT AND TRADEMARK OFFICE
CERTIFICATE OF CORRECTION

PATENT NO. : 6,040,147  
APPLICATION NO. : 09/054212  
DATED : March 21, 2000  
INVENTOR(S) : Ridker et al.

Page 1 of 1

It is certified that error appears in the above-identified patent and that said Letters Patent is hereby corrected as shown below:

On the first line under the title, add the following paragraph:

GOVERNMENT SUPPORT

Some aspects of the present invention were made with support by grants from the United States National Institutes of Health (NIH) under NIH grants HL26490, HL34595, HL46696, CA34944, CA42182, and CA40360. The U.S. Government may retain certain rights in the invention.

Signed and Sealed this

Twenty-fifth Day of March, 2008

JON W. DUDAS  
*Director of the United States Patent and Trademark Office*